United States Patent
Siffert (12)

(10) Patent No.: US 6,242,181 B1
(45) Date of Patent: Jun. 5, 2001

(54) METHODS FOR DIAGNOSING HYPERTENSION BY DETECTING A MUTATION IN THE HUMAN G PROTEIN β3 SUBUNIT GENE

(75) Inventor: Winfried Siffert, Schönleinstr, 49, Essen (DE)

(73) Assignee: Winfried Siffert, Essen (DE)

( * ) Notice: Subject to any disclaimer, the term of this patent is extended or adjusted under 35 U.S.C. 154(b) by 0 days.

(21) Appl. No.: 09/180,783

(22) PCT Filed: May 2, 1997

(86) PCT No.: PCT/EP97/02250

§ 371 Date: Mar. 17, 1999

§ 102(e) Date: Mar. 17, 1999

(87) PCT Pub. No.: WO97/43442

PCT Pub. Date: Nov. 20, 1997

(30) Foreign Application Priority Data

May 14, 1996 (DE) ............................................. 196 19 362

(51) Int. Cl.[7] ............................. C12Q 1/68; C12P 19/34; C07H 21/04
(52) U.S. Cl. ........................... 435/6; 435/91.2; 536/23.5; 536/24.31
(58) Field of Search ..................... 435/6, 91.2; 536/23.5, 536/24.31

(56) References Cited

PUBLICATIONS

Kato et al. Hypertension. 32:935–938, 1998.*
Brand et al. Hypertension. 33:1175–1178, 1999.*
Town et al. American Journal of Medical Genetics. 88:465–468, 1999.*
Fogarty et al. Diabetologia. 41:1304–1308, 1998.*
R.G.H. Cotton, Current Methods of Mutation Detection, Mutation Research, vol. 285, Jan. 1, 1993, pp. 125–144.
Michael A. Levine et al., Molecular Cloning of Beta3 Subunit, a Third Form of the G Protein Beta–Subunit Polypeptide, Proc. Antl. Acad. Sci., vol. 87, 1990, pp. 2329–2333.
Winfried Siffert et al., Enhanced G Protein Activation in Immortalized Lymphoblasts From Patients With Essential Hypertension, J. Clin. Invest., vol. 96, 1995, pp. 759–766.

* cited by examiner

Primary Examiner—Carla J. Myers
(74) Attorney, Agent, or Firm—Nixon Peabody LLP; David S. Safran

(57) ABSTRACT

A method of diagnosing a disease comprising determining the presence of a genetic modification in a gene obtained from a subject which encodes a human G protein β3 subunit. Also disclosed is a method for establishing the relative risk of developing a disorder associated with G protein dysregulation.

7 Claims, 1 Drawing Sheet

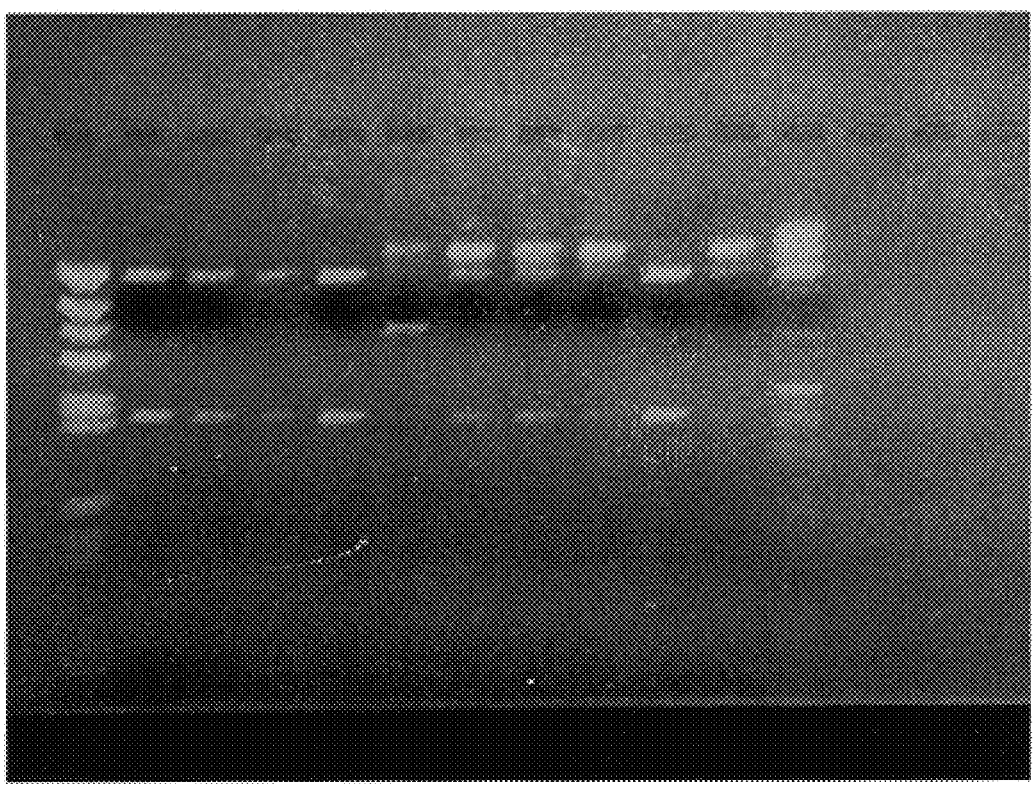

SEQUENCE LISTING

<160> NUMBER OF SEQ ID NOS: 4

<210> SEQ ID NO: 1
<211> LENGTH: 1517
<212> TYPE: DNA
<213> ORGANISM: Homo sapiens

<400> SEQUENCE: 1
atgggggaga tggagcaact gcgtcaggaa gcggagcagc tcaagaagca gattgcagat     60

-continued

```
gccaggaaag cctgtgctga cgttactctg gcagagctgg tgtctggcct agaggtggtg      120
ggacgagtcc agatgcggac gcggcggacg ttaagggac  acctggccaa gatttacgcc      180
atgcactggg ccactgattc taagctgctg gtaagtgcct cgcaagatgg gaagctgatc      240
gtgtgggaca gctacaccac caacaaggtg cacgccatcc cactgcgctc ctcctgggtc      300
atgacctgtg cctatgcccc atcagggaac tttgtggcat gtggggggct ggacaacatg      360
tgttccatct acaacctcaa atcccgtgag gcaatgtca  aggtcagccg ggagctttct      420
gctcacacag gttatctctc ctgctgccgc ttcctggatg acaacaatat tgtgaccagc      480 tcggggggaca ccacgtgtgc cttgtgggac attgagactg ggcagcagaa gactgtattt     540
gtgggacaca cgggtgactg catgagcctg gctgtgtctc ctgacttcaa tctcttcatt      600 tcggggggcct gtgatgccag tgccaagctc tgggatgtgc gagagggac  ctgccgtcag     660 actttcactg ccacgagtc  ggacatcaac gccatctgtt tcttcccaa  tggagaggcc      720 atctgcacgg gctcggatga cgcttcctgc cgcttgtttg acctgcgggc agaccaggag      780
ctgatctgct ctcccacga  gagcatcatc tgcggcatca cgtctgtggc cttctccctc      840
agtggccgcc tactattcgc tggctacgac gacttcaact gcaatgtctg ggactccatg      900
aagtctgagc gtgtgggcat cctctctggc cacgataaca gggtgagctg cctgggagtc      960
acagctgacg ggatggctgt ggccacaggt tcctgggaca gcttcctcaa aatctggaac     1020
tgaggaggct ggagaaaggg aagtggaagg cagtgaacac actcagcagc ccctgcccg      1080 accccatctc attcaggtgt tctcttctat attccgggtg ccattcccac taagctttct     1140
cctttgaggg cagtggggag catgggactg tgcctttggg aggcagcatc agggacacag     1200
gggcaaagaa ctgcccatc  tcctcccatg gccttccctc cccacagtcc tcacagcctc     1260
tcccttaatg agcaaggaca acctgcccct ccccagccct tgcaggccc  agcagacttg     1320 agtctgaggc cccaggccct aggattcctc cccagagcc  actacctttg tccaggcctg     1380
ggtggtatag ggcgtttggc cctgtgacta tggctctggc accactaggg tcctggccct     1440
cttcttattc atgctttctc cttttttctac cttttttttct ctcctaagac acctgcaata    1500
aagtgtagca ccctggt                                                    1517
```

```
<210> SEQ ID NO: 2
<211> LENGTH: 340
<212> TYPE: PRT
<213> ORGANISM: Homo sapiens

<400> SEQUENCE: 2

Met Gly Glu Met Glu Gln Leu Arg Gln Glu Ala Glu Gln Leu Lys Lys
 1               5                  10                  15

Gln Ile Ala Asp Ala Arg Lys Ala Cys Ala Asp Val Thr Leu Ala Glu
            20                  25                  30

Leu Val Ser Gly Leu Glu Val Val Gly Arg Val Gln Met Arg Thr Arg
        35                  40                  45

Arg Thr Leu Arg Gly His Leu Ala Lys Ile Tyr Ala Met His Trp Ala
    50                  55                  60

Thr Asp Ser Lys Leu Leu Val Ser Ala Ser Gln Asp Gly Lys Leu Ile
65                  70                  75                  80

Val Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110
```

```
Ala Cys Gly Gly Leu Asp Asn Met Cys Ser Ile Tyr Asn Leu Lys Ser
            115                 120                 125

Arg Glu Gly Asn Val Lys Val Ser Arg Glu Leu Ser Ala His Thr Gly
        130                 135                 140

Tyr Leu Ser Cys Cys Arg Phe Leu Asp Asp Asn Asn Ile Val Thr Ser
145                     150                 155                 160

Ser Gly Asp Thr Thr Cys Ala Leu Trp Asp Ile Glu Thr Gly Gln Gln
                165                 170                 175

Lys Thr Val Phe Val Gly His Thr Gly Asp Cys Met Ser Leu Ala Val
            180                 185                 190

Ser Pro Asp Phe Asn Leu Phe Ile Ser Gly Ala Cys Asp Ala Ser Ala
            195                 200                 205

Lys Leu Trp Asp Val Arg Glu Gly Thr Cys Arg Gln Thr Phe Thr Gly
            210                 215                 220

His Glu Ser Asp Ile Asn Ala Ile Cys Phe Phe Pro Asn Gly Glu Ala
225                 230                 235                 240

Ile Cys Thr Gly Ser Asp Asp Ala Ser Cys Arg Leu Phe Asp Leu Arg
                245                 250                 255

Ala Asp Gln Glu Leu Ile Cys Phe Ser His Glu Ser Ile Ile Cys Gly
            260                 265                 270

Ile Thr Ser Val Ala Phe Ser Leu Ser Gly Arg Leu Leu Phe Ala Gly
            275                 280                 285

Tyr Asp Asp Phe Asn Cys Asn Val Trp Asp Ser Met Lys Ser Glu Arg
            290                 295                 300

Val Gly Ile Leu Ser Gly His Asp Asn Arg Val Ser Cys Leu Gly Val
305                 310                 315                 320

Thr Ala Asp Gly Met Ala Val Ala Thr Gly Ser Trp Asp Ser Phe Leu
                325                 330                 335

Lys Ile Trp Asn
            340

<210> SEQ ID NO: 3
<211> LENGTH: 20
<212> TYPE: DNA
<213> ORGANISM: Homo sapiens

<400> SEQUENCE: 3
tgggggagat ggagcaactg                                              20

<210> SEQ ID NO: 4
<211> LENGTH: 21
<212> TYPE: DNA
<213> ORGANISM: Homo sapiens

<400> SEQUENCE: 4
ctgctgagtg tgttcactgc c                                            21
```

METHODS FOR DIAGNOSING HYPERTENSION BY DETECTING A MUTATION IN THE HUMAN G PROTEIN β3 SUBUNIT GENE

BACKGROUND OF THE INVENTION:

(i) Field of the Invention

The present invention relates to a method for the diagnosis of diseases by genetic analysis, in particular the analysis of genes for subunits of the human guanine nucleotide-binding proteins (G proteins).

(ii) Description of the Related Art

Heterotrimeric guanine nucleotide-binding proteins (G proteins) have an outstanding importance in intracellular signal transduction. They mediate the relaying of extracellular signals after stimulation of hormone receptors and other receptors which undergo a conformational change after receptor activation. This leads to activation of G proteins which may subsequently activate or inhibit intracellular effectors (eg. ion channels, enzymes). Heterotrimeric G proteins consist of three subunits, the α, β and γ subunits. To date, several different α subunits, 5 β subunits and about 12 γ subunits have been detected by biochemical and molecular biological methods (Binbaumer, L. and Bimnbaumer, M. Signal transduction by G proteins: 1994 edition. *J.Recept.Res.* 15:213–252, 1995; Offermanns, S. and Schultz, G. Complex information processing by the transmembrane signaling system involving G proteins. *Naunyn Schmiedebergs Arch.Pharmacol.* 350:329–338, 1994; N Ürnberg, B., Gudermann, T., and Schultz, G. Receptors and G proteins as primary components of transmembrane signal transduction. Part 2. G proteins: structure and function. *J.Mol.Med.* 73:123–132, 1995; Neer, E. J. Heterotrimeric G proteins: Organizers of Transmembrane Signals. *Cell* 80:249–257, 1995;. Rens-Domiano, S. and Hamm, H.E. Structural and functional relationships of heterotrimeric G-proteins. FASEB J. 9:1059–1066, 1995).

Receptor-medi ated activation of certain α subunits can be inhibited by pretreatment with pertussis toxin (PTX). These include, in particular, the α isoforms αi1, αi2 and αi3, and various oα subunits. G proteins of these types are also referred to as PTX-sensitive G proteins.

SUMMARY OF THE INVENTION-

We have found that a genetic modification in the gene for human G protein β3 subunits is suitable for the diagnosis of diseases. This genetic modification is particularly suitable for establishing the risk of developing a disorder associated with G protein dysregulation.

The invention furthermore relates to a method for establishing a relative risk of developing disorders associated with G protein dysregulation for a subject, which comprises comparing the gene sequence for an G protein β3 unit of the subject with the gene sequence SEQ ID NO:1, and, in the event that a thymine (T) is present at position 825, assigning the subject an increased risk of disease.

BRIEF DESCRIPTION OF THE DRAWING:

FIG. 1 depicts a comparison of genes from normotensives and hypertensives by restriction enzyme analysis.

DETAILED DESCRIPTION OF PREFERRED EMBODIMENTS:

The genetic modification which has been found is located in the gene for human G protein β33 subunit. This gene has been described by Levine et al. (Proc. Natl. Acad. Sci USA, 87, (1990) 2329–2333). The coding region has an Ser codon (TCC) at position 275, while subjects with an increased risk of a disease associated with G protein dysregulation have the codon TCT, which likewise codes for Ser, at this position. The genetic modification is a base substitution at position 825 in which a cytosine (C) is replaced by thymine (T). However, this base exchange is "silent" at the amino-acid level, ie. it does not lead to incorporation of a different amino acid at this position. The sequence found in subjects with an increased risk of disease is depicted in SEQ ID NO:1 in the sequence listing.

The genetic modification which has been found usually occurs in heterozygous form.

Disorders associated with G protein dysregulation are defined as diseases in which the G protein is involved in signal transduction and does not carry out its function in a physiological manner.

The dysregulation may have a number of causes, for example a modification in the structural gene or modified gene expression.

The disorders include cardiovascular diseases, metabolic disturbances and immunological diseases.

Cardiovascular diseases which may be mentioned are:

Hypertension, pregnancy hypertension (gestosis, hypertension in pregnancy), coronary heart disease, localized and/or generalized atherosclerosis, stenoses of blood vessels, restenosis after revascularizing procedures (eg. PTCA with and without stent implantation), tendency to stroke or thrombosis and increased platelet aggregation.

Metabolic disturbances which may be mentioned are:

Metabolic syndrome, insulin resistance and hyperinsulinemia, type II diabetes mellitus, diabetic complications (eg. nephropathy, neuropathy, retinopathy, etc.) disturbances of lipid metabolism, disturbances of central chemoreception ($CO_2$ tolerance, acidosis tolerance, sudden infant death (SIDS)).

Immunological diseases which may be mentioned are:

Impaired strength of the body's immune response (formation of immunoglobulins, aggressiveness of T cells and NK cells), impaired general tendency to proliferation, including wound-healing capacity, tendency to develop tumors and proliferation including metastasizing potential of malignantly transformed cells, duration of the latency period after HIV infection until the disease becomes clinically evident, Kaposi sarcoma, tendency to cirrhosis of the liver, transplant tolerance and transplant rejection.

The use of the genetic mutation according to the invention is particularly suitable for establishing the risk of developing hypertension.

The invention furthermore relates to the production of transgenic animals harboring the genetic mutation described above. Transgenic animals of this type are of great importance in particular as animal models for the investigation and therapy of the disorders described above. The methods for generating transgenic animals are generally known to the skilled worker.

For the method according to the invention for establishing the relative risk of developing a disease, body material containing the subject's genetic information is taken from a subject. This is achieved as a rule by taking blood and isolating the nucleic acid therefrom.

The structure of the gene for the G protein β3 subunit is established from the subject's isolated nucleic acid and is compared with the sequence indicated in SEQ ID NO:1.

The structure of the gene can be established by sequencing of the nucleic acid. This can take place either directly from the genomic DNA or after amplification of the nucleic acid, for example by the PCR technique.

The structure of the gene can take place at the genomic level or else at the mRNA or cDNA level.

It is preferably established by sequencing after PCR amplification of the cDNA. The primers suitable for the PCR can easily be inferred by the skilled worker from the sequences depicted in SEQ ID NO:1 The procedure foo this is advantageously such that in each case a primer binding a strand and complementary strand in front of and behind the relevant base position 825 is chosen.

However, other methods can also be used for comparison of the genes, for example selective hybridization or appropriate mapping with restriction enzymes. The C→T base exchange at the position 825 described. above leads to loss of a cleavage site for the restriction enzyme Dsa I, which is likewise used to detect this genetic polymorphism.

If the subject ha s a thymine (T) at position 825, he is to be assigned a greater risk of disease than a subject with a cytosine (C) at this position.

The invention is illustrated further in the following examples.

EXAMPLE 1

Detection of the genetic modification in hypertensives by sequencing

An enhanced susceptibility to activation of PTX-sensitive G proteins was detected in preliminary investigations on patients with essential hypertension. This detection was possible in immortalized cells from patients having as phenotypical marker an enhanced activity of the Na/H exchanger. The enhanced susceptibility to activation of PTX-sensitive G proteins has important consequences for cellular function. These include enhanced formation of intracellular second messenger molecules (eg. inositol 1,4,5-trisphosphate), enhanced release of intracellular $Ca^{2+}$ ions, increased formation of immunoglobulins and an increased rate of cell growth. Since these changes can be detected in immortalized cells and after a long duration of cell culturing, it may be assumed that this modification is genetically fixed (Rosskopf, D., Frömter, E., and Siffert, W. Hypertensive sodium-proton exchanger phenotype persists in immortalized lymphoblasts from essential hypertensive patients-a cell culture model for human hypertension. *J.Clin.Invest.* 92:2553–2559, 1993; Rosskopf, D., Hartung, K., Hense, J., and Siffert, W. Enhanced immunoglobulin formation of immortalized B cells from hypertensive patients. *Hypertension* 26:432–435, 1995; Rosskopf, D., Schröder, K.-J., and Siffert, W. Role of sodium-hydrogen exchange in the proliferation of immortalised lymphoblasts from patients with essential hypertension and normotensive subjects. *Cardiovasc.Res.* 29:254–259, 1995; Siffert, W., Rosskopf, D., Moritz, A , Wieland, T., Kaldenberg-Stasch, S., Kettler, N., Hartung, K., Beckmann, S., and Jakobs, K.H. Enhanced G protein activation in immortalized lymphoblasts from patients with essential hypertension. *J.Clin.Invest.* 96:759–766, 1995).

RNA was prepared by standard methods from immortalized cell lines from hypertensives and was transcribed into cDNA using reverse transcriptase. Using the polymerase chain reaction (PCR), the cDNA coding for the G protein β3 subunit was amplified and sequenced. The following oligonucleotide primers were employed for the PCR:
5'-TGG GGG AGA TGG AGC AAC TG and
5'-CTG CTG AGT GTG TTC ACT GCC.

Compared with the sequence published by Levine et al. (Levine, M. A., Smallwood, P. M., Moen, P. T.,Jr., Helman, L.J., and Ahn, T. G. Molecular cloning of β3 subunit, a third form of the G protein β-subunit polypeptide. *Proc. Natl. Acad. Sci. USA* 87(6):2329–2333, 1990), the following difference was found in the cDNA from hypertensives' cells: nucleotide 825 cytosine (C) in the region of the coding sequence is replaced by a thymine (T) (nucleotide 1 corresponds to base A in the ATG start codon). This base exchange leads to a silent polymorphism, ie. the amino acid encoded by the corresponding base triplet (serine) is not altered by comparison with the original sequence. The DNA sequence found is described in SEQ ID NO:1.

EXAMPLE 2

Detection of the genetic modification in hypertensives by restriction enzyme analysis The figure depicts a comparison of genes from normotensives and hypertensives by restriction enzyme analysis. In this, the cDNA coding for β3 from cells from normotensives (NT) and hypertensives (HT), which had been amplified by PCR, was subjected to a restriction enzyme analysis using the enzyme Dsa I. The reaction roducts were fractionated in an agarose gel, which is depicted in the figure.

The complete restriction of β3 cDNA from normotensive cells after digestion with Dsa I is clearly evident from the figure. The cDNA from hypertensives' cells is only partly cut by Dsa I. Apart from the cleavage products to be expected there is also uncleaved PCR product. Reference fragments (markers) are loaded on the left and right for comparison of sizes. Four of the five DNA sequences from hypertensives depicted here show the base exchange described above and are heterozygous for this modification.

We claim:

1. A method for diagnosing an increased likelihood of hypertension in a human subject comprising determining the presence of a genetic modification in a gene obtained from said subject which encodes a human G protein $\beta_3$ subunit by comparing said gene to the gene sequence of SEQ ID NO: 1, wherein said genetic modification is a substitution of cytosine by thymine at position 825 in SEQ ID NO: 1, wherein the presence of said genetic modification is associated with an increased likelihood of hypertension.

2. The method as claimed in claim 1, wherein the presence of a genetic modification in the gene obtained from a subject is determined by sequencing.

3. The method as claimed in claim 2, further comprising the step of amplifying the gene obtained from the subject before sequencing.

4. The method as claimed in claim 2, wherein at least a portion of the gene obtained from the subject is amplified, said portion including the third nucleotide, of the codon that encodes the amino acid at position 275 of said human G protein $\beta_3$ subunit.

5. The method as claimed in claim 1, wherein the presence of a genetic modification in the gene obtained from the subject is determined by hybridization.

6. The method as claimed in claim 1, wherein the presence of a genetic modification in the gene obtained from the subject is determined by cleavage using a restriction enzyme.

7. The method as claimed in claim 6, wherein the restriction enzyme is Dsa I.

* * * * *